United States Patent [19]

Jimbow

[11] Patent Number: 5,395,611
[45] Date of Patent: Mar. 7, 1995

[54] PHENOLIC AMINE DEPIGMENTING AND ANTIMELANOMA AGENTS

[75] Inventor: Kowichi Jimbow, Edmonton, Canada

[73] Assignee: The Governors of the University of Alberta, Edmonton, Canada

[21] Appl. No.: 873,688

[22] Filed: Apr. 24, 1992

Related U.S. Application Data

[63] Continuation of Ser. No. 513,273, Apr. 24, 1990, abandoned.

[51] Int. Cl.6 .................. A61K 7/135; A61K 31/135; A61F 2/02
[52] U.S. Cl. ..................................... 424/62; 424/423; 424/59; 514/649
[58] Field of Search .................. 514/630, 649; 424/62, 424/63, 59, 422, 423, 712; 564/219, 341

[56] References Cited

U.S. PATENT DOCUMENTS

| | | | |
|---|---|---|---|
| 4,134,996 | 1/1979 | Dunbar et al. | 514/654 |
| 4,183,927 | 1/1980 | Begin et al. | 514/239.2 |
| 4,246,201 | 1/1981 | Borzatta | 564/317 |
| 4,545,982 | 10/1985 | Takahashi | 514/784 |

FOREIGN PATENT DOCUMENTS

| | | |
|---|---|---|
| 3410070A1 | 10/1985 | Germany . |
| 1561679 | 2/1980 | United Kingdom . |

OTHER PUBLICATIONS

F. Alena, K. Jimbow, S. Ito, "Melanocytotoxicity and Antimelanoma Effects of Phenolic Amine Compounds in Mice in Vivo," Cancer Res., 50(12):3743–7 (1990).

S. Inoue, S. Ito, K. Wakamatsu, K. Jimbow, K. Fujita, "Mechanism of Growth Inhibition of Melanoma Cells by 4–S–Cysteaminylphenol and its Analogs," Biochem. Pharmacol., 39(6):1077–83 (1990).

H. Herman, S. Pollock, L. Fowler, S. May, "Demonstration of the Potent Antihypertensive Activity of Phenyl–2–Aminoethyl Sulfides," J. Cardiovasc. Pharmacol., 11(5):501–10 (1988).

S. Padgette, H. Herman, J. Han, S. Pollock, S. May, "Antihypertensive Activites of Phenyl Aminoethyl Sulfides, a Class of Synthetic Substrates for Dopamine β–Hydroxylase," J. Med. Chem., 27(10):1354–7 (1984).

E. Karaulova, T. Bobruiskaya, G. Galpern, V. Nikitina, L. Shekhoyan, A. Koshevnik, "Reaction of Arylthiacyclanylsulfonium Salts with Nitrogenous Bases. Synthesis of Aminoalkylarylsulfides," Khim. Geterotsikl. Soedin., (6):759–64 (1975)(Russ.).

F. Alena, J. Pankovich, K. Jimbow, "Melanocytotoxicity and Enzyme Kinetics of Cysteaminylphenol and its Derivatives," 2nd WHO Melanoma Conference, Oct. 16–19, 1989.

F. Alena, K. Jimbow, J. Pankovich, S. Ito, "Cytotoxic Effects of 4–S–Cysteaminylphenol and Its N–Acetyl Derivative on Melanocytes and Melanoma Cells in Vivo,"2nd Meeting, PanAmerican Society for Pigment Cell Research, Apr. 23–26, 1989.

F. Alena, K. Jimbow, J. Pankovich, S. Ito, "N–Acetyl–4–S–Cysteaminylphenol, a new Phenolic Melanin Precursor and Melanocytotoxicity," Meeting of Amer. Soc. for Clin. Inves., Apr. 1989.

(List continued on next page.)

Primary Examiner—Thurman K. Page
Assistant Examiner—Carlos Azpuru
Attorney, Agent, or Firm—Finnegan, Henderson, Farabow, Garrett & Dunner

[57] ABSTRACT

A composition useful for treating skin pigmentation, melasma and melanoma comprises:
i) a biologically effective amount of derivatives of 4-S-cysteaminylphenyl such as N-acetyl-4-S-cysteaminylphenol, α-methyl-4-S-cysteaminylphenol, N,N'-dimethyl-4-S-cysteaminylphenol and 4-S-homocysteaminylphenol; and
ii) a suitable biologically compatible carrier for the selected active compound.

38 Claims, No Drawings

OTHER PUBLICATIONS

S. Inoue et al., Mechanism of Growth Inhibition of Melanoma Cells by 4-S-Cysteaminylphenol and its Analogues, Biochem. Pharm., 39(6):1077-1083(1990).

J. Pankovich et al., 4-S-Cysteaminylphenol and its Analogues as Substrates for Tyrosinase and Monoamine Oxidase, Munksgaard, Pigment Cell Research, 3:146-149(1990).

Miura et al., "Synthesis of Cysteinylphenol, Cysteaminylphenol, and Related Compounds, and In Vivo Evaluation of Antimelanoma Effect", Arch. Dermatol. Res. (1987) 279:219-225.

Ito et al., "Depigmentation of Black Guinea Pig Skin by Topical Application of Cysteaminylphenol, Cysteinylphenol, and Related Compounds", The Journal of Investigative Dermatology, vol. 88, No. 1, Jan. 1987.

Icke, R. N. et al., "Preparation of B-phenylethyldimethylamine", Org. Syn. Coll. 3:723-725, 1955.

Ito et al, "Selective Cytotoxicity of 4-S-Cysteaminylphenol on Follicular Melanocyte of the Black Mouse: Rational Basis for its Application to Melanoma Chemotherapy", Cancer Research, Jun. 15, 1987 47:3278-3284.

Padgette et al., Journal of Medicinal Chemistry, 1984 27:1354-1367.

PHENOLIC AMINE DEPIGMENTING AND ANTIMELANOMA AGENTS

This application is a continuation of application Ser. No. 07/513,273, filed Apr. 24, 1990, now abandoned.

FIELD OF THE INVENTION

This invention relates to compositions useful in blocking melanin synthesis in human or animal melanocyte cells. More particularly, the compositions are useful in treating pigmentation due to a variety of skin disorders, including skin cancer in the form of melanoma.

BACKGROUND OF THE INVENTION

Pigmentary diseases are often characterized in the elevated levels of the enzyme tyrosinase in melanocytes; i.e., human and animal cells which synthesize the pigment melanin. There are a variety of pigmentary diseases, such as melasma, melanoma, moles and the like. In particular, moles are susceptible to becoming melanoma after exposure to sunlight which results in increased synthesis of tyrosinase.

Usually commercial forms of depigmenting compositions are based on the use of hydroquinone. However, the hydroquinone preparations are very unstable and cause skin irritation. Hydroquinone compositions can also cause permanent whitening of the skin if used for a prolonged period and at a high concentration. As to treatment of melanoma, this is presently attended to by surgical procedures, since any type of known non-surgical treatment of melanoma is unsatisfactory.

Research work has been conducted in the field of phenolic and diphenolic compounds to serve as a basis for chemotherapeutic treatment of melanoma and skin depigmentation. In particular, 4-S-cysteinylphenol (4-S-CP) and 4-S-cysteaminylphenol (4-S-CAP) have been synthesized and evaluated for cytotoxicity to normal epidermal melanocytes to determine their effectiveness as depigmenting agents and antimelanoma agents. Miura et al, "Synthesis of Cysteinylphenol, Cysteaminylphenol, and Related Compounds, and In Vivo Evaluation of Antimelanoma Effect", Arch. Dermatol Res. (1987) 279:219–225, discloses the effect of 4-S-CAP and 4-S-CP in depigmentation of black hair as manifested by loss of functioning melanocytes. The effectiveness of these compounds was compared against the use of hydroquinone to achieve depigmentation. It was established that 4-S-CAP was a potent agent in prolonging the lifespan of melanoma-bearing mice and hence exhibited inhibition of melanoma growth. The 4-S-CP and the methyl ester of 4-S-CP also exhibited some inhibition of melanoma growth, although not as active as the 4-S-CAP.

The same compounds, 4-S-CP and 4-S-CAP, were also investigated for properties of depigmentation of black guinea pig skin by topical application. The results of this work is reported by Ito et al, "Depigmentation of Black Guinea Pig Skin by Topical Application of Cysteaminylphenol, Cysteinylphenol, and Related Compounds", The Journal of Investigative Dermatology, Vol. 88 No. 1, January 1987. Although the 4-S-CAP demonstrated depigmenting properties, inflammatory changes of the skin of the guinea pigs was prominent. The 4-S-CAP was capable, however, of:

1. decreasing the number of functioning melanocytes;
2. decreasing the amount of epidermal melanin pigments; and
3. degenerating and destroying melanocytes.

4-S-CP and 4-S-CAP were also investigated for their selective cytotoxicity on follicular melanocytes. This was reported by Ito et al, "Selective Cytotoxicity of 4-S-Cysteaminylphenol on Follicular Melanocyte of the Black Mouse: Rational Basis for its Application to Melanoma Chemotherapy", Cancer Research, Jun. 15, 1987 47:3278–3284. It was reported that 4-S-CAP demonstrated cytotoxicity in the depigmentation of black hair follicles, whereas it had no effect on the albino follicles. Hence 4-S-CAP is actively engaged in the melanin synthesis of the melanocytes.

The 4-S-CAP compound, however, has several limitations from the standpoint of practical clinical use. These limitations include:

a. hypotensive effect; and
b. high toxicity due to the 4-S-CAP being a substrate for monoamineoxidase (MAO) which in the plasma converts 4-S-CAP into an aldehyde form which produces a non-specific cytotoxicity.

SUMMARY OF THE INVENTION

In accordance with an aspect of this invention, a composition is useful for blocking melanin synthesis in human or animal melanocyte cells. In one embodiment, this composition is useful where synthesis of melanin is associated with skin pigmentation, melasma and melanoma. Such composition is not a substrate for the MAO pathway. The composition comprises:

i) a biologically effective amount of an active compound selected from the group represented by the formula:

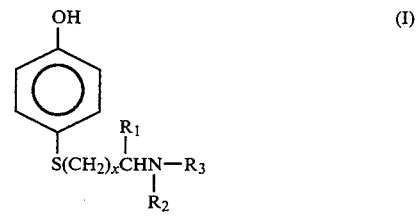

wherein
$R_1$ is H or lower alkyl;
$R_2$ is H or lower alkyl;
$R_3$ is H, lower alkyl or lower alkanoyl, and
x is 1 to 5
with the proviso that when x is 1 one of $R_1$, $R_2$ or $R_3$ is other than H; and ii) a suitable biologically compatible carrier for the selected active compound.

According to a preferred aspect of the invention, this composition is particularly useful as a depigmenting composition in sunscreening lotions. The composition is also useful as an antimelanoma agent and useful for the treatment of melasma.

According to another aspect of the invention, a method is provided for blocking melanin synthesis in human or animal melanocyte cells of skin. This method comprises:

i) treating human or animal Skin by use of a composition comprising a biologically effective amount of an active compound selected from the group represented by the formula:

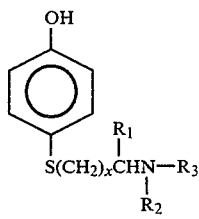

wherein
R$_1$ is H or lower alkyl;
R$_2$ is H or lower alkyl;
R$_3$ is H, lower alkyl or lower alkanoyl, and
x is 1 to 5
with the proviso that when x is 1, one of R$_1$, R$_2$ or R$_3$ is other than H and ii) the selected active compound being used in a suitable biologically compatible carrier.

In one embodiment, this method is useful where the synthesis of melanin is associated with skin pigmentation, melasma and melanoma. Such methods of treatment are preferably applied in the depigmenting of skin due to UV exposure, melasma and is also useful in the treatment of melanoma.

According to another aspect of the invention, in a method of formulating a composition useful for blocking melanin synthesis in human or animal melanocyte cells of skin, the method includes mixing:

i) a biologically effective amount of an active compound selected from the group represented by the formula:

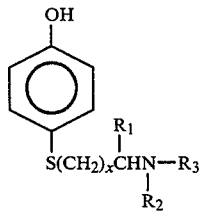

wherein
R$_1$ is H or lower alkyl;
R$_2$ is H or lower alkyl;
R$_3$ is H, lower alkyl or lower alkanoyl, and
x is 1 to 5
with the proviso that when x is 1, one of R$_1$, R$_2$ or R$_3$ is other than H ii) the selected active compound being used in a suitable biologically compatible carrier. In one embodiment, this method is useful where the synthesis of melanin is associated with skin pigmentation, melasma and melanoma.

DETAILED DESCRIPTION OF THE PREFERRED EMBODIMENTS

Compositions, according to this invention, are useful in treating a variety of pigmentary diseases with which synthesis of melanin is associated. For example, the compositions are useful for treating pigmentary diseases, such as melasma, melanoma and other skin cancers and prevention of melanoma and other pigmentary diseases, such as caused by exposure to sunlight. The composition, according to this invention, exhibits considerably less toxicity than the known form of phenolic amine compounds, such as 4-S-CP and 4-S-CAP. The active compounds, which are used in the composition of this invention, are selected from the group of compounds represented by formula I:

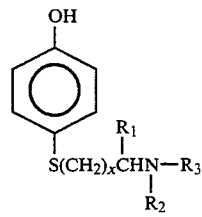

wherein
R$_1$ is H or lower alkyl;
R$_2$ is H or lower alkyl;
R$_3$ is H, lower alkyl or lower alkanoyl, and
x is 1 to 5
with the proviso that when x is 1, one of R$_1$, R$_2$ or R$_3$ is other than H.

Preferred compounds of the invention of Formula I are represented by the following compound matrix:

| Compound | R$_1$ | R$_2$ | R$_3$ | X |
| --- | --- | --- | --- | --- |
| α-methyl-4-S-CAP | CH$_3$ | H | H | 1 |
| N,N'-dimethyl-4-S-CAP | H | CH$_3$ | CH$_3$ | 1 |
| N-Ac-4-S-CAP | H | H | COCH$_3$ | 1 |
| 4-S-homo-CAP | H | H | H | 2 |

The compounds, according to this invention, may be manufactured in a variety of synthesis techniques. Generally, the preparation of in particular 4-S-CAP is in accordance with the technique disclosed by Ito et al, "Synthesis of Cysteinylphenol, Cysteaminylphenol, and Related Compounds, and in vivo Evaluation of Antimelanoma Effect", supra. This entails the reaction of a phenol with a cysteamine to yield the 4-S-cysteaminylphenol or the 2-S-cysteaminylphenol. The 4-S-cysteaminylphenol may then be isolated from the reaction product by melting point separation. It is understood that the various derivatives of this invention may be made by various radical substitutions to the sulphur chain, or substituting a thiol with the desired chain.

A proposed method for the manufacture of the compounds of this invention may be via the Weirmeister reaction. This process is described in Padgette et al, Journal of Medicinal Chemistry, 1984 27:1354-1357. The reaction scheme is as follows:

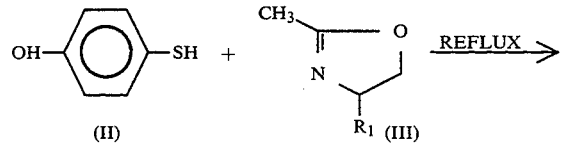

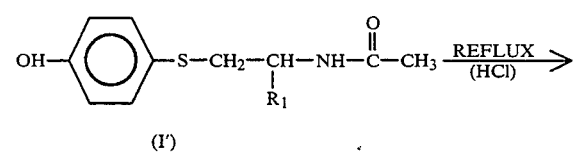

-continued

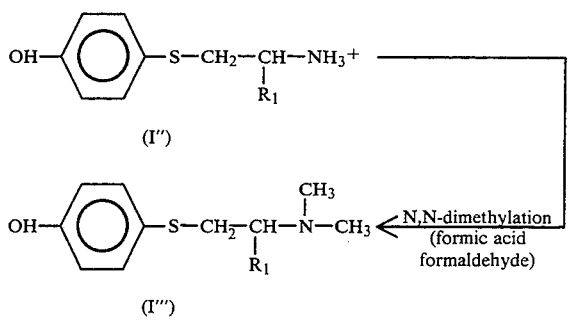

(I'')

(I''')

wherein for preferred compounds of this invention:
i) $R_1$ is H in formula (III) to yield N-Ac-4-S-CAP in formula (I');
ii) $R_1$ is $CH_3$ in formula (III) to yield α-Me-4-S-CAP in formula (I''); and
iii) $R_1$ is H in formula (III) to yield N,N-dimethyl-4-S-CAP in formula (I''').

Other compounds of the invention may be made in accordance with the above procedures where $R_1$ and reactant (III) are substituted, as one skilled in the art would appreciate, to synthesize compounds of the invention within the scope of the selected substituents for $R_1$, $R_2$, $R_3$ and x. Details of processes for making some of the preferred compounds of the invention are set out in the accompanying Examples.

The compositions of this invention provide a mechanism for treating a variety of pigmentary diseases, such as melasma, melanoma and other skin cancers and preventing melasma and skin cancers which are normally induced by exposure to UV radiation. This activity of the composition is achieved by the selected active compound of the composition becoming toxic in the melanocytes in the presence of tyrosinase.

Pigment cell metabolic pathway is unique as it pertains to the conversion of tyrosine and dopa with subsequent formation of the pigment polymer melanin. This is accomplished in the presence of the enzyme tyrosinase. This pathway is present only in melanocytes and its malignant counterpart. The enzyme tyrosinase is at very high level of concentration in malignant melanoma as well as in active pigment cells. This pathway, however, does not serve any other essential role in the human or animal, so that active agents, according to this invention, need not discriminate between normal and malignant cells. Previous attempts to impair the melanin pathway as a therapeutic strategy have had limited success, because the hydroquinones as previously used were unstable and not sufficiently active in the pathway at physiologically tolerable levels. Similar problems have been encountered with the use of 4-S-CAP to inhibit the growth of melanoma cells and destroy melanocytes by interfering with the melanin pathway. However, 4-S-CAP is hypotensive and has high toxicity at low doses. As already discussed, 4-S-CAP is a substrate not only for tyrosinase, but also for plasma monoamineoxidase (MAO). It has been demonstrated that 4-S-CAP is converted by plasma MAO into an aldehyde form which produces non-specific cytotoxicity in the host. The agents, according to the composition of this invention, do not, however, provide a substrate for plasma MAO, but are substrates for tyrosinase. The compositions, according to this invention, have significant melano cytotoxicity and antimelanoma effects. This is recognized in the significant depigmentation of hair on black experimental animals, as well as significantly inhibiting the experimental growth of lung metastases of B16 F10 melanoma cells. The compositions of this invention have also demonstrated selective toxicity to other neural crest tumours, such as pheochromocytoma and neuroblastoma cells.

In view of these variety of uses of the composition of this invention in treatment of pigmentary diseases, melanoma and for use in sunscreen compositions, it is appreciated that the compositions may be in solution or of a cream nature for applications in the treatment. Accordingly, the composition of this invention, as broadly applied in blocking melanin synthesis in human or animal melanocyte cells, comprises:
a biologically effective amount of the active compound selected from the group of formula I is administered in combination with a suitable biologically compatible carrier for the selected active compound.

With reference to the compounds of formula I, experimental tests on animals indicate per single dose toxicity levels in the range of 1,400 mg/kg of body weight for N-Acetyl-4-S-CAP and 500 mg/kg of body weight per single dose for α-methyl-4-S-CAP.

In these compositions, a biologically effective amount of the active compound is understood by those skilled in the art to mean that a sufficient amount of the compound in the composition is provided such that upon administration to the human or animal by, for example, i.p., s.c. or topical route provides sufficient active agent on each application to give the desired result in treating pigmentary diseases, melanoma, melasma, or acting as UV blocker and/or depigmenting agent in sunscreen lotions. However, the biologically effective amount of the active compound is at a level that it is not toxic to the human or animal during the term of treatment. By a suitable biologically compatible carrier, it is understood by those skilled in the art that the carrier may be a solution for the compound when the compound is injected by either i.p. or s.c. route. When the compound is topically applied, it is understood that the carrier may be any type of suitable excipient or carrier in the form of cosmetic compositions, pharmaceutical adjuvants, sunscreen lotions and the like.

Suitable biologically compatible carriers for injection include physiologically normal saline and other types of readily injectable solutions which are well understood by those skilled in the art. The preferred injectable carrier is neutral buffer having a pH of 7.0 to 7.4.

Suitable carriers for topical application include conventional skin treatment compositions, such as cosmetic compositions and pharmaceutical preparations. Examples of such ingredients for topical application are oils such as liquid paraffin, vaseline, methyl-polysiloxane, castor oil, squalane, and coconut oil; anti-oxidants such as butylated hydroxyanisole, butylhydroxytoluene, ethyl gallate, and tocopherol; surfactants such as sodium laureate, laurylpyridinium chloride, polyoxyethylene sorbitan monooleate, glyceryl monoarachate, sodium N-stearyl-N,N-dimethyl glycine, oleyl hydrolysed animal protein, and polyoxypropylene glyceryl ether phosphate; humectants such as glycerol, sodium 2-pyrrolidone-5-carboxylate, and sodium lactate; thickeners such as tragacanth gum, quince seed gum, zanthan gum, carboxyvinyl polymer and bentonite; preservatives such as benzoic acid, allyl p-hydroxybenzoates, dehydroacetic acid and trichlorocarbonilide; colouring agents and pigments such as Acid Red Rhodamine B, Violamin R, Orange SS, Naphthol, Yellow-S, Tartrazine, Alizarin, Cyanine Green F, Brilliant Blue CFC, Acid Violet, Carthamine, β-carotene, Red, Blue & Yellow Oxide of Iron, titatium dioxide, Yellow Iron Oxide, Cobalt Blue, Ultramarine Blue, Rose & Violet, tri-iron tetroxide, and carbon black; waxes such as Bees wax, Japan wax, Carnauba wax, Candelilla wax, and lanolin; film-forming agents such as nitrocellulose and polyvinyl alcohol; solvents or dispersing media such a water and alcohols (e.g. ethanol); powders such as aluminum powder, talc, kaolin, zinc oxide, titanium dioxide, mica, calcium, carbonate, and treated powders; plasticizers such as acetyl tributyl citrate, and dibutylphthalate; pharmaceutically active agents such as retinol, palmitate; γ-orizanol, pyridoxine dipalmitate, ascrobyl dipalmitate, ergocalciferol, di-α-tocopherol acetate, biotin, ethinylestradoil estrone, hydrocrotisone, calcium pantothenate, ammonium glycyrrhizinate, allantoid, quaiasulene, and hinokitiol; and perfumes such as musk, civet, amber, jasmine absolute, and rose oil.

The skin treatment composition, according to this invention, can be prepared in any conventional form, for example, solubilized forms such as cosmetic lotions, and emulsified forms such as liquid creams, creams, ointments and dispersions.

The compositions of this invention can then be further characterized as a composition particularly useful for depigmenting skin where the composition is applied topically or injected by s.c. or i.p. route to the afflicted area to achieve desired degree of depigmentation of the skin. Hence as another aspect of the invention, the composition is useful in the method of treating skin for purposes of depigmentation. As well, the invention provides for formulating a composition which is useful for depigmenting skin.

The composition of the invention is also useful for treating melanoma. The composition is administered either topically or by injection through i.p. or s.c. route. According to a method of the invention, the application of the composition for treating the melanoma to clear it up or place it in remission. Furthermore, a method of the invention is in the formulating of the composition useful for treating melanoma.

The composition may be used in sunscreening lotions where the biologically compatible carrier for the depigmenting agents of the invention. It has been found that the active agents:

1. prevent UV radiation activating melanin synthesis in melanocytes;
2. prevent moles from becoming melanoma after exposure to sunlight; and
3. react as a substrate for the enzyme tyrosinase which substrate is an active agent of the compound of formula I in producing toxic components which act as depigmenting agents and possibly as UV blockers in the sunscreen lotion.

Quite surprisingly, it has been found that N-Ac-4-S-CAP of this invention is an extremely potent depigmenting agent causing 90% depigmentation in treated areas by either the i.p. or s.c. route of administration. The N-Ac-4-S-CAP exhibits in addition greater antimelanoma effects in reducing melanoma lung colonies to 25% of original volume. Compared to, for example, 4-S-CAP, this is quite surprising. 4-S-CAP with regard to antimelanoma properties effectively reduced melanoma lung colonies to 30% of the controls. As to depigmentation, the 4-S-CAP compound only achieves 87% depigmentation by the i.p. route of administration and a very low 47% depigmentation by the s.c. route of administration.

For purposes of treatment, it is understood that depending upon the route of administration the composition of this invention may have various concentrations of active agent in the biologically compatible carrier. For purposes of injection, the concentration of the active agent in the injectable solution is in the range of 200 to 1200 mg/kg of body weight with a preferred dosage in the range of 300 mg to 500 mg/kg of body weight. For purposes of topical application, the concentration of the active agent in the cosmetic cream or the like is in the range of 4% to 10% by weight in a cream base with a preferred composition in the range of 4% to 6% by weight in a cream base.

It is appreciated that various complementary agents may be included with the active agents of this invention. For example, the composition may be administered in combination with L-dopa and/or antidecarboxylase. Such combinations may have selected use in the treatment of various melanomas.

The following Examples demonstrate various aspects of the invention in providing treatment of pigmentation diseases, depigmenting properties and antimelanoma properties. Although the Examples demonstrate effectiveness in this area for only some of the compounds of formula I, it is understood that the compounds of formula I all exhibit in a predictable way similar properties.

EXAMPLE 1

Enzyme Kinetics for Tyrosinase and Monoamineoxidase

Mushroom tyrosinase (400 units/mg) and plasma MAO (1000 units/gm) were obtained from Sigma Chemical Co. (St. Louis, Mo., USA). A reaction mixture consisted of a substrate of 7 to 8 different concentrations (40 to 500 μM for mushroom tyrosinase and 20 to 200 μM for MAO) and of either mushroom tyrosinase (2.5 μg) or MAO (10 μg) in 1.0 mL of 0.05M sodium phosphate buffer, pH 6.8 and 7.4 respectively. The reactions were carried out at 37° C. in a shaking water bath, and stopped by taking 100 μL of the reaction mixture and adding it to 900 μL of 0.4M $HCLO_4$. The disappearance of substrate was followed using HPLC (high pressure liquid chromatography) Km and Vmax values were calculated from the Lineweaver-Burk plots.

Similar to 4-S-CAP, N-acetyl-4-S-CAP is also a tyrosinase substrate as demonstrated in the following Table 1.

TABLE 1

ENZYME KINETICS OF 4-S-CAP AND N-Ac-4-S-CAP WITH TYROSINASE AND MONOAMINEOXIDASE (MAO)

| Substrate | Tyrosinase[a] | | MAO[b] | |
|---|---|---|---|---|
| | Km | V max | Km | V max |
| 4-S-CAP | 117 | 7.97 | 52.6 | 143 |
| N-Ac-4-S-CAP | 1000 | 10.1 | — | 0.0 |

[a]mushroom tyrosinase; 11 unit/ml of tyrosinase was used. One enzyme unit will cause an increase in A280 of 0.001 per min at pH 6.8 at 25° C. using L-tyrosine as substrate.
[b]plasma monoamine oxidase: 0.005 unit/ml of MAO was used. One enzyme unit will oxidize 1.0 μM of benzylamine to benzaldehyde per min at pH 7.6 at 25° C.

The maximum rate of reaction with tyrosinase is much higher with N-Ac-4-S-CAP than 4-S-CAP. N-Ac-4-S-CAP is not, however, a substrate for plasma MAO, whereas 4-S-CAP is a substrate for both plasma MAO and tyrosinase.

EXAMPLE 2

Administration of Compound of this Invention to Determine Toxicity Levels Compared to 4-S-CAP Details of experimental chemotherapy with synthetic compounds have been outlined in the protocol of Geran et al "Protocols for Screening Chemical Agents and Natural Products Against Animal Tumours and Other Biological Systems" (3rd ed.), Cancer Chemother Rep. 3:1–85 1972. In accordance with this Protocol, ten to fifteen mice were used in each test group. They were weighed and randomized at day one after s.c. inoculation of B16 melanoma cells. From day five, the phenolic melanin precursors were administered i.p. daily for nine days. The test compounds were dissolved in normal saline, and sterilized by heating to 100° C. for 2 minutes. They were stable under this treatment as judged by HPLC assay (Muira et al, "Synthesis of Cysteinylphenol, Cysteaminylphenol, and Related Compounds, and In Vivo Evaluation of Antimelanoma Effect" supra). They were administered j.p. with the following doses: 400 mg/Kg - 4-S-CAP; 200 to 300 mg/Kg - 4-S-CAP; and 200 to 1200 mg/Kg - N-Ac-4-S-CAP. A catalytic amount of L-dopa, 25 mg/Kg and antidecarboxylase, carbidopa, 400 mg/Kg, were also administered. Carbidopa was given one hour prior to L-dopa administration. DTIC (NSC 4538) was used as a control drug at a dose of 60 mg/Kg. Acute toxicity of 4-S-CP and 4-S-CAP was evaluated from 100 to 1600 mg/Kg. The lethal dose was found to be 600 mg/Kg and 400 mg/Kg in 4-S-CP and 4-S-CAP respectively (Miura et al, "Synthesis of Cysteinylphenol, Cysteaminylphenol, and Related Compounds, and In Vivo Evaluation of Antimelanoma Effect" supra). The homologue, N-Ac-4-S-CAP, was 1400 mg/Kg.

EXAMPLE 3

Evaluation of In Vivo Inhibition of B16 Melanoma between 4-S-CAP and N-Ac-4-S-CAP In accordance with Example 2, the maximum tolerable dose of 4-S-CAP and N-Ac-4-S-CAP by single i.p. injection is in the range of 200 to 300 ml/Kg and 1200 ml/Kg of body weight respectively. The B16 mouse melanoma was maintained by s.c. inoculation of tumour cells into the back of C57BL7J mice (5 to 6 weeks, female). The details of tumour preparation and growth characteristics have been previously reported in Miura et al, "Synthesis of Cysteinylphenol, Cysteaminylphenol, and Related Compounds, and In Vivo Evaluation of Antimelanoma Effect" (supra). Briefly, excised tumours were homogenized in normal saline. The homogenized tumour cells were then passed through a sterile 80 mesh stainless steel screen, washed with normal saline, centrifuged (500 g. for 10 minutes) and resuspended in normal saline. Suspensions of viable melanoma cells at the concentration of $1 \times 10^6$ per 0.1 ml were inoculated s.c. into both the right and left inguinal areas of C57BL/6J mice (female, 5 to 6 weeks old, 18 to 20 gm).

The in vivo antimelanoma effect of the compounds were evaluated by percent growth inhibition of inoculated tumour (% g.i.). The percent g.i. was computed from the mean tumour volume at day 12 or 13 of the experiments; i.e., $100 \times$ (1- treated group/control group). Tumour volume was calculated by the following formula:

tumour volume = long axis × (short axis)$^2$ × ½.

N-Ac-4-S-CAP showed a dose-dependent linear growth inhibition (Table 2). In one experiment (experiment I) 4-S-CAP showed a greater anti-melanoma effect at 200 mg/Kg than N-Ac-4-S-CAP. To further examine whether a minimal does of N-Ac-4-S-CAP, 200 mg/Kg has an antimelanoma effect, three groups of mice were treated with N-Ac-4-S-CAP. All of the test groups revealed a significant reduction in size of s.c. inoculated melanoma as compared to that treated with normal saline. One of the advantages of N-Ac-4-S-CAP over 4-S-CAP was that it had much higher $LD^{50}$ (as high as 1400 mg/Kg of body weight, and therefore a greater range of safety).

TABLE 2

IN VIVO GROWTH INHIBITION (GI) OF B16 MELANOMA BY N-ACETYL-4-S-CYSTEAMINYLPHENOL (N-Ac-4-S-CAP)

| COMPOUNDS | Dose (mg/Kg) | Number of animals | Tumour Volume (mm$^3$) | % Gi | T-Test |
|---|---|---|---|---|---|
| EXPERIMENT I | | | | | |
| Normal saline | — | 10 | 520 ± 76 | — | — |
| 4-S-CAP | 200 | 10 | 239 ± 39 | 54.0 | p < 0.05 |
| N-Ac-4-S-CAP | 200 | 10 | 313 ± 83 | 39.8 | NS |
| N-Ac-4-S-CAP | 400 | 10 | 222 ± 13 | 57.3 | p < 0.01 |
| N-Ac-4-S-CAP | 600 | 10 | 192 ± 48 | 63.18 | p < 0.01 |
| N-Ac-4-S-CAP | 800 | 11 | 133 ± 11 | 74.4 | p0.001 |
| EXPERIMENT II | | | | | |
| Normal saline | — | 10 | 544 ± 54 | — | — |
| 4-S-CAP | 200 | 10 | 405 ± 61 | 25.1 | NS |
| N-Ac-4-S-CAP | 200 | 10 | 370 ± 37 | 32.0 | p < 0.01 |
| N-Ac-4-S-CAP | 400 | 10 | 359 ± 52 | 34.0 | p < 0.05 |
| N-Ac-4-S-CAP | 800 | 11 | 199 ± 26 | 63.4 | P < 0.01 |
| N-Ac-4-S-CAP | 1200 | 8 | 159 ± 23 | 70.7 | p < 0.001 |

EXAMPLE 4

Assay of Melanoma-Colony Formation in the Lungs Impact of 4-S-CAP and N-Acetyl-4-S-CAP Murine B16F10 melanoma cell line with a strong metastatic property to form tumour colonies in the lungs was obtained from Dr. Longenecker, Department of Immunology, University of Alberta. Such cell line is well recognized and readily available as reported in Miura et al, supra. The cells were grown in T-75 flasks in dulbecco's MEM available from Gipco Lab Inc., Grand Island, N.Y., supplemented with 10% fetal calf serum, also obtained from Gipco, penicillin (100 μ/ml) and streptomycin (100 μg/ml). The cells were incubated at 37° C. in humidified atmosphere of 5% $CO_2$ in air. The cells were harvested by applying a thin layer of 0.25% trypsin solution in EDTA, washed and resuspended in cold N saline solution. Viable cells were identified by trypan blue dye exclusion and counted. The cell suspension was diluted to the desired concentration. Three groups of mice were studied using a control 4-S-CAP and N-Ac-4-S-CAP as the active agents in the treatment. On day zero, the mice were inoculated via the lateral tail vein with $5 \times 10^4$ cells in 0.2 ml of N saline. The test drugs were dissolved in normal saline, sterilized by membrane filtration, and administered in a dose of 300 mg/Kg (4-S-CAP) or 900 mg/Kg (N-Ac-4-S-CAP); starting on day five, the control solution or drug was injected i.p. daily for 14 days. On day 26, the mice were killed by cervical dislocation, their lungs were removed, and the number of melanoma colonies was counted under a dissecting microscope. The results were expressed as percentage reduction in the number of colonies: $[a-b/a] \times 100$, where a=colonies in control group and b=colonies in experimental group.

The numbers of B16F10 melanoma colonies were significantly reduced after treatment with N-Ac-4-S-CAP and 4-S-CAP as shown in Table 3.

TABLE 3

ANTIMELANOMA EFFECTS OF 4-S-CYSTEAMINYL-PHENOL AND N-ACETYL-4-S-CYSTEAMINYLPHENOL ON THE FORMATION OF B16F10 MELANOMA COLONIES IN MOUSE LUNGS EXCISED 26 DAYS AFTER INJECTION OF THE CELL SUSPENSION

| Compound | No. of Mice | No. of Colonies per pair of lungs | % control | t Test (P) |
|---|---|---|---|---|
| Normal saline soln (control) | 10 | 86.5 ± 32.9 | 100.0 | — |
| 4-S-CAP, 300 mg/kg | 10 | 28.0 ± 14.5 | 32.4 | <0.001 |
| N-Ac-4-S-CAP, 900 mg/kg | 10 | 21.5 ± 10.8 | 24.9 | <0.001 |

Examination under a dissecting microscope revealed marked reduction in size of those tumours remaining (diameter 1.5–1.7 mm vs. 2.5–3.1 mm in controls) and marked depigmentation or melanosis of some of the tumours. The only side effects in this administration as noted were briefly apathy and mild hyperthermia immediately after i.p. injection. Average body weight was the same on day zero and at time of death.

EXAMPLE 5

Metabolic Assays for 4-S-CAP and N-Ac-4-S-CAP

Fifteen mice randomly divided into three groups of five were injected i.p. with a test agent (300 mg/kg) dissolved in N saline solution. Group 1 were injected with 4-S-CAP, group 2 with N-Ac-4-S-CAP, group 3 were controls. The mice are kept in metabolic cages; their urine is collected 3, 8 and 24 hr after injection, and the 4-S-CAP and N-Ac-4-S-CAP content is measured by HPLC in a system consisting of a Waters 600E liquid chromatography, with a Bondapak C18 column (3.0×300 mm; particle size, 10 μm) and a Waters 460 electrochemical detector. Mobile phase: 0.1M potassium phosphate buffer, pH 2.1, containing 0.1 mM $Na_2EDTA$ methanol, 80:20 (v/v); column temperature, 60° C.; flow rate 1.0 ml/min. Urine samples are hydrolysed with 0.1M HCl before assay, and the phenols are detected at 850 mV against an Ag/AgCl reference electrode.

Urinary excretion of the unchanged compounds, without conversion or degradation, was maximal 3 h after i.p. injection (5.2 mg/mouse), this was 7.7% (0.399±0.018 mg) for 4-S-CAP and 13.9% (0.723±0.027 ng) for N-Ac-4-S-CAP. Later excretion of these two compounds, respectively, was as follows: at 8 h, 8.5% (0.443±0.023 mg) and 19.8% (1.034±0.033 mg); and at 24 h, 8.8% (0.458±0.021 mg) and 20.4% (1.089±0.028 mg). Most notably, 1.3% (0.066±0.003 mg) of the N-Ac-4-S-CAP i.p. dose was excreted as 4-S-CAP, indicating conversion to the mother compound of part of this homolog administered by this route.

EXAMPLE 6

Depigmentation and Melanomacytotoxicity Characteristics

Breeding pairs of C57BL/6J black mice were purchased from Jackson Laboratory, Bar Harbor, Ma. Female progeny were used in this testing when approximately 8 weeks old and weighing 17 grams.

Black hairs were plucked manually from the back of the mice to initiate new anagen growth and activate follicular melanocytes with increased tyrosinase activity. Thirty mice were randomized into 6 groups of 5 (1 control and 1 for each compound). Starting on day 1, daily for 14 days the agent was injected i.p. or was infiltrated s.c. in an area where hair follicles had been plucked; the dose was 300 mg/kg body weight.

In the same 30 mice, hair follicles were harvested on day 22 (early telogen phase) and their eumelanin content analyzed. Details of the assay, including chemical degration of melanin and high-performance liquid chromatography (HPLC) were as described in Ito et al, "Quantitative Analysis of Eumelanin and Pheomelanin in Hair and Melanosomes" J. Invest. Dermatol 80:268–272, 1983. Briefly, a 10-mg hair sample is homogenized in water at a concentration of 10 mg/ml; the 200-μl homogenate is transferred to a screw-capped test tube, mixed with 1M $H_2SO_4$ (800 μL) and oxidized with 3% $KMnO_4$. The product, pyrrole-2,3,5-tricarboxylic acid (PTCA), is analyzed by HPLC with a UVL detector; samples are measured in duplicate. The eumelanin content is expressed as PTCA (ng/mg) against the PCTA content of BALB/c albino mice as control ($\leq 10$ ng/mg, the background value with our method, in which 1 ng corresponds roughly to a eumelanin content of 50 ng), and the degree of depigmentation is expressed as a percentage: (PTCA content of control sample minus PTCA content of experimental sample)/(PCTA content of control sample)×100.

Depigmentation of new growth of black hair follicles was most marked after injection of N-Ac-4-S-CAP whether it be by i.p. or s.c. route. The new hair was almost pure white as in albino mice. For the remaining compounds tested, the degree of depigmentation with other phenolic amine compounds was α-Me-4-S-CAP>4-S-CAP>4-S-HomoCAP, and N,N-DiMe-4-S-CAP the lowest. Depigmentation after s.c. injection N-Ac-4-S-CAP was similar with doses of 600 and 300 mg/kg. With 4-S-CAP and α-ME 4-S-CAP, i.p. administration induced more depigmentation than s.c., whereas 4-S-HomoCAP induced much more depigmentation when given s.c. than i.p. N,N-Di-Me-4-S-CAP induced no visible changes in pigmentation in new follicles.

No side-effects of the compounds were apparent. The most potent depigmentation agent was N-Ac-4-S-CAP, which induced 98% depigmentation in new growing follicles by both i.p. and s.c. administration and with little or no dose-related difference in degree as shown in Table 4. There was no statistically significant difference in melanin content between hair follicles with N-Ac-4-S-CAP and control albino mice. α-Me-4-S-CAP induced 89% depigmentation after i.p. injection and 58% after s.c. administration, and the latter caused some irritation of the skin in the plucked area. The depigmentation potency of 4-S-CAP was similar to that of α-Me-4-S-CAP, being 87% after i.p. and 47% after s.c. administration. Interestingly, 4-S-HomoCAP evidenced greater potency when given s.c. (63.5%) than i.p. (12.1%), this was higher than with 4.S-CAP, α-Me-4-S-CAP and N,N-DiMe-4-S-CAP given s.c. N,N-DiMe-4-S-CAP induced no significant depigmentation when given p.i. or s.c. (7.3% and 6.1% respectively).

TABLE 4

PTCA CONTENT AND DEPIGMENTATION OF NEW HAIR AFTER TREATMENT WITH PHENOLIC AMINE COMPOUNDS

| Compound Injected (300 mg/kg) | PTCA Content (ng/mg) | Depigmentation (%) | t Test (P) |
|---|---|---|---|
| Route: i.p. | | | |
| N saline soln (control) | 1089.4 ± 48.9 | 0.0 | — |
| N-Ac-4-S-CAP | 26.0 ± 10.3 | 97.6 | <0.001 |
| α-Me-4-S-CAP | 121.3 ± 81.9 | 88.9 | <0.001 |
| 4-S-CAP | 146.1 ± 72.4 | 86.6 | <0.001 |
| 4-S-HomoCAP | 956.7 ± 77.9 | 12.1 | >0.05 |
| N,N-DiMe-4-S-CAP | 1009.0 ± 193.5 | 7.3 | >0.02 |
| Route s.c. | | | |
| N saline soln (control) | 1089.4 ± 48.9 | 0.0 | — |
| N-Ac-4-S-CAP | 30.8 ± 9.1 | 97.2 | <0.001 |
| α-Me-4-S-CAP | 557.9 ± 47.2 | 57.9 | <0.001 |
| 4-S-CAP | 458.3 ± 107.6 | 46.9 | <0.001 |
| 4-S-HomoCAP | 397.7 ± 279.3 | 63.5 | >0.02 |
| N,N-DiMe-4-S-CAP | 1023.4 ± 110.1 | 6.1 | >0.2 |

EXAMPLE 7

Light and Electron Microscopy of Melanocytes

In six groups of 4 mice (1 control and 1 for each compound) were treated daily with the control or compound injected i.p. The compounds tested were 4-S-CAP, N-Ac-4-S-CAP and α-Me-4-S-CAP. Samples of skin and regrowing hair follicles were excised under brief general anaesthesia on day 10 (late anagen phase), fixed in Karnovsky's solution (2.5% glutaraldehyde and 2.5% paraformaldehyde in 011M cacodylate buffer), and refixed in 1% osmium tetroxide in cadodylate buffer. Tissues were stained en bloc with 1.5% uranyl acetate in o.1M veronal buffer for 30 min, dehydrated in graded ethanol solutions, embedded in epoxy resin, and sectioned with a Potter-Blum ultramicrotome MT II. Sections 1.0 µm thick were stained with methylene blue for light microscopy, thin sections were stained with led citrate for electron microscopy.

In control samples, there were melanocytes in the bulb above the hair's papilla and both melanocytes and surrounding keratinocytes were filled with black pigment. On day 10, after N-Ac-4-S-CAP given i.p., neither functioning melanocytes nor melanin pigments remained in the follicles but there were no vacuolar changes in cells of the hair bulk, and after α-Me-4-S-CAP i.p. there was a similar loss of functioning melanocytes and melanin pigments. By contrast, after i.p. injection of 4-S-CAP, the hair follicles contained functioning melanocytes and melanin pigments transferred into keratonocytes, although they were much sparser than in the controls.

In the electron microscopy examination, after i.p. injection for 10 days, no melanocytes or melanosomes were visible after treatment with N-Ac-4-S-CAP, whereas the follicles contained variable number of functioning melanocytes and melanosomes after injection of the other compounds. Melanocytes from mice treated with α-Me-4-S-CAP and 4-S-CAP contained immature melanosomes at stages II and III, whereas those from controls were full of mature melanosomes at stage IV.

These results demonstrate that N-Ac-4-S-CAP and α-Me-4-S-CAP possess the greatest cytotoxicity for follicular depigmentation. This indicates the selective melanocytotoxicity of these compounds as they relate to melanin synthesis and tyrosinase activity which is at its highest in plucked hair. These compounds demonstrate low toxicity as they are not involved in plasma MAO activity. Furthermore the compounds demonstrate potent antimelanoma characteristics. In view of the low toxicity of these compounds and their depigmenting and antimelanoma properties, they constitute excellent choices in compositions of this invention for treatment of pigmentary disease, such as melasma, treatment of melanoma and for use in sunscreen compositions.

EXAMPLE 8

Synthesis of N-AC-4-S-CAP

A mixture of 2-methyl-2-oxazoline (16.9 mL, 0.197 mol) and 4-mercaptophenol (24.85 g, 0.197 mol) was heated under reflux (neat) for 2 h at about 130° C. under Ar (spontaneous heating occurred upon mixing). Upon cooling of the reaction mixture to 0° C., a white solid precipitated, which was collected and recrystallized from dilute EtOH to give a white product (36.2 g, 87%): mp 123°–125° C.; $^1$H NMR [(CD$_3$)$_2$=O]δ6.99 (d,d, 4 H) , 3.50–2.60 (m, 5 H), 1.87 (s, 3 H); mass spectrum (EI) , m/e 211 (M+), (CI) m/e 212 (M+1). Anal. (C$_{10}$H$_{13}$NO$_2$S) C,H,N.

EXAMPLE 9

Synthesis of 4-S-HomoCAP

A general method for preparing 3-thiopropylamine derivatives [Kawase, M. et al "Mode of Action of 3-Substituted Propylamine Cytotoxicity in Culture Cells" Biochem Pharmacol,31:2983–2988, 1982] was adapted as follows. A mixture of 4-mercaptophenol (1.0 g, 7.9 mmol) and acrylonitrile (0.69 mL, 10.3 mmol) in ethanol (2 mL) was refluxed for 6 hr under an argon atmosphere in the presence of 25% trimethylphenylammonium hydroxide (0.2 mL). After cooling, the mixture was diluted with water and extracted with chloroform (2×50 mL). The combined organic extracts were dried (Na$_2$SO$_4$) and concentrated to give a solid. Purification by column chromatography on silica gel (chloroform:ethylacetate, 30:1) afforded colourless crystals of a nitrile 1.25 g, 88%): m.p. 72°–73° (from benzene).

A solution of the nitrile (1.0 g, 5.6 mmol) in ether (5 mL) was added slowly to a vigorously stirred suspension of lithium aluminum hydride (0.48 g, 12.6 mmol) in ether (7 mL) at 0° under an argon atmosphere. The mixture was then refluxed for 3 hr under an argon atmosphere. After cooling in ice, ethyl acetate and then a saturated solution of potassium sodium tartrate were added. The mixture was filtered and the precipitate was washed with ethyl acetate and then with methanol. The combined filtrates were concentrated to give an oily residue which was dissolved in 6M HCl (20 ml) and extracted with ether (30 mL). The aqueous phase was evaporated to dryness and the residue was chromatographed on Dowex 50W-X2 ® (2.0×16 cm) and eluted with 3M HCl (15 mL/fraction). Evaporation of fractions 68, 120 left the CHl salt of 4-S-HomoCAP which was dissolved in water and adjusted to pH 9 with conc. ammonia to give colourless crystals of 4-S-HomoCAP (0.31 g, 30%); m.p. 139°–141°. Anal. Calcd. for C$_9$H$_{13}$NOS; C, 58.98; J, 7.15; N, 7.64; S, 17.49%. Found: C, 58.87; H, 7.10; N, 7.66; S, 17.38%.

EXAMPLE 10

Synthesis of α-Me-4-S-CAP

The method of Padgette et al, "Antihypertensive Activities of Phenol Aminoethyl Sulfides, a Class of Synthetic Substrates for Dopamine β-hydroxylase", J. Med. Chem. 27:1354–1367, 1984, was modified as follows. To a mixture of ethyl orthoacetate (3.57 g, 47.5 mmol) and 1,2-dichloroethane (20mL) was added 2-amino-1-propanol (7.7 g, 47.5 mmol). The resulting solution was refluxed for 9 hr under an argon atmosphere. After cooling, 4-mercaptophenol (5.0 g, 39.5 mmol) was added to the reaction mixture and was heated under reflux for 16 hr at ca. 130° under an argon atmosphere. The resulting mixture was evaporated in a rotary evaporator. The remaining solid was crystallized by adding benzene to a hot chloroform solution of the amide to give crystals of α-Me-N-acetyl-4-S-CAP (6.25 g, 70%). The amide (6.25 g, 27.8 mmol) was refluxed in 6M (HCl (110 ml) for 24 hr under an argon atmosphere. After cooling, the solution was extracted with ether (2×50 ml) and the aqueous phase was evaporated to dryness. The residue was dissolved in water (100 ml) and the solution was adjusted to pH 9 with conc. ammonia to give colourless crystals of a α-Me-4-S-CAP (4.0 g, 78%); p.m. 105°–106°. Anal. Calcd. for $C_9H_{13}NOS$; C, 58.98; H, 71.5; N, 7.64; S, 17.49%. Found C. 58.75; H, 7.16; N, 7.56; S, 17.04%.

EXAMPLE 11

Synthesis of N,N-DiMe-4-S-CAP

A common procedure of N,N-dimethylation of primary amines [Icke, R. N. et al "Preparation of β-phenyl-ethyldimethylamine" Org. Syn. Coll. 3:723–725, 1955] was adapted. A mixture of 4-S-CAP (6.76 g 40 mmol), 98% formic acid (15.2 mL, 400 mmol), and 37% formaldehyde (18.0 ml, 240 mmol) was heated under reflux for 1 hr. After cooling, 6M HCl (10 ml) was added and the mixture was evaporated in a rotary evaporator. The residue was dissolved in water (200 ml) and the solution was adjusted to pH 8 with conc. ammonia. The precipitated brown oil was decanted off and the supernatant was then adjusted to pH 9 to give pale yellow crystals of N,N-DiMe-4-S-CAP (4.3 g, 55%): m.p. 115°–116°. Anal. Calcd. for $C_{10}H_{13}NOS$: C, 60.88; H, 7.66; N, 7.10; S. 16.25%. Found: C. 60.61; H, 7.71; N, 7.05; S, 16.34%.

Although preferred embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. A composition for use in blocking melanin synthesis in human or animal melanocyte cells comprising:
   (i) a melanin synthesis-blocking amount of an active compound selected from the group of compounds represented by the formula (I):

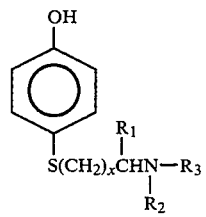

wherein
$R_1$ is H or $C_1$ to $C_8$ alkyl;
$R_2$ is H;
$R_3$ is H, $C_1$ to $C_8$ alkyl or $C_1$ to $C_8$ alkanoyl, and x is 1 to 5
with the proviso that $R_1$ or $R_3$ is other than H; and
   (ii) a suitable biologically compatible carrier for the selected active compound.

2. A composition of claim 1, wherein said active compound is selected from the group consisting of N-acetyl-4-S-cysteaminylphenol cysteaminylphenol, 4-S-homo-cysteaminylphenol and α-methyl-4-S-cysteaminylphenol.

3. A composition of claim 2, wherein said carrier is normal saline solution whereby said composition is injectable by subcutaneous route or intraperitoneal route.

4. A composition of claim 1, wherein said a melanin synthesis-blocking amount does not exceed 1400 mg/Kg of body weight per single dose.

5. A composition of claim 3, wherein said a melanin synthesis-blocking amount does not exceed 500 mg/kg of body weight per single dose.

6. A composition for use in treating hyperpigmentation comprising:
   (i) a depigmenting effective amount of an active compound selected from the group of compounds represented by the formula (I):

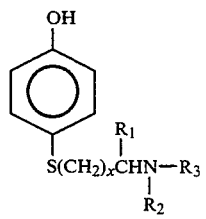

wherein
$R_1$ is H or $C_1$ to $C_8$ alkyl;
$R_2$ is H;
$R_3$ is H or $C_1$ to $C_8$ alkyl or $C_1$ to $C_8$ alkanoyl, and x is 1 to 5
with the proviso that $R_1$ or $R_3$ is other than H; and
   (ii) a suitable biologically compatible carrier for the selected active compound.

7. A depigmenting composition of claim 6, wherein said active compound is selected the group consisting of N-acetyl-4-S-cysteaminylphenol and α-methyl-4-S-cysteaminylphenol.

8. A depigmenting composition of claim 6, wherein said carrier is a topical carrier whereby said depigmenting agent may be applied topically.

9. A depigmenting composition of claim 8, wherein said carrier is a sunscreening composition whereby said depigmenting agent is applied topically.

10. A depigmenting composition of claim 6, wherein said carrier is a biologically compatible solution whereby said composition is injectable by subcutaneous route or intraperitoneal route.

11. A depigmenting composition of claim 6, said selected depigmenting agent is selective in destroying melanocyte cells in human or animal body without becoming a substrate for monoamine oxidase.

12. A depigmenting composition of claim 6 useful in the treatment of melasma wherein said carrier is selected from the group consisting of an injectable solution or a topical carrier.

13. A composition for use in treating melanoma comprising:
(i) an anti-melanoma effective amount of an active compound selected from the group of compounds represented by the formula (I):

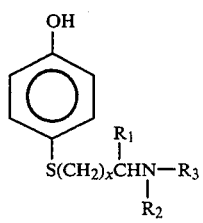
(I)

wherein
$R_1$ is H or $C_1$ to $C_8$ alkyl;
$R_2$ is H;
$R_3$ is H or $C_1$ to $C_8$ alkyl or $C_1$ to $C_8$ alkanoyl, and x is 1 to 5
with the proviso that $R_1$ or $R_3$ is other than H; and
(ii) a suitable biologically compatible carrier for the selected active compound.

14. An antimelanoma composition of claim 13 wherein said carrier is an injectable solution.

15. An antimelanoma composition of claim 13 wherein said active compound is selected from the group consisting of N-acetyl-4-S-cysteaminylphenol and α-methyl-4-S-cysteaminylphenol.

16. An antimelanoma composition of claim 13 wherein said anti-melanoma effective amount does not exceed 1400 mg/kg body weight per single dose.

17. An antimelanoma composition of claim 13 wherein said carrier is a topical carrier.

18. A composition of claim 2, wherein said active compound is N-acetyl-4-S-cysteaminylphenol.

19. A depigmenting composition of claim 7, wherein said active compound is N-acetyl-4-S-cysteaminylphenol.

20. A topical pharmaceutical composition comprising:
(i) an active compound selected from the group of compounds represented by the formula (I):

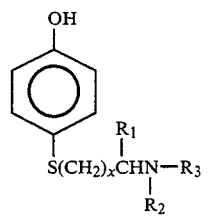
(I)

wherein
$R_1$ is H or $C_1$ to $C_8$ alkyl;
$R_2$ is H;
$R_3$ is H, $C_1$ to $C_8$ alkyl or $C_1$ to $C_8$ alkanoyl, and x is 1 to 5
with the proviso that $R_1$ or $R_3$ is other than H; and
(ii) a pharmaceutically acceptable topical carrier for the selected active compound.

21. A topical pharmaceutical composition of claim 20, wherein said active compound is selected from the group consisting of N-acetyl-4-S-cysteaminylphenol and α-methyl-4-S-cysteaminylphenol.

22. A topical pharmaceutical composition of claim 21, wherein said active compound is N-acetyl-4-S-cysteaminylphenol.

23. A topical pharmaceutical composition of claim 20, wherein said carrier is a sunscreening composition.

24. A topical pharmaceutical composition of claim 21, wherein said carrier is a sunscreening composition.

25. A topical pharmaceutical composition of claim 22, wherein said carrier is a sunscreening composition.

26. A composition of claim 1 wherein $R_1$ is $C_1$ to $C_8$ alkyl and $R_2$ and $R_3$ are H.

27. A composition of claim 1 wherein $R_3$ is $C_1$ to $C_8$ alkanoyl and $R_1$ and $R_2$ are H.

28. A composition of claim 2 wherein said active compound is α-methyl-4-S-cysteaminylphenol.

29. A depigmenting composition of claim 6 wherein $R_1$ is $C_1$ to $C_8$ alkyl and $R_2$ and $R_3$ are H.

30. A depigmenting composition of claim 6 wherein $R_3$ is $C_1$ to $C_8$ alkanoyl and $R_1$ and $R_2$ are H.

31. A depigmenting composition of claim 7 wherein said active compound is α-methyl-4-S-cysteaminylphenol.

32. An anti-melanoma composition of claim 13 wherein $R_1$ is $C_1$ to $C_8$ alkyl and $R_2$ and $R_3$ are H.

33. An anti-melanoma composition of claim 13 wherein $R_3$ is $C_1$ to $C_8$ alkanoyl and $R_1$ and $R_2$ are H.

34. An anti-melanoma composition of claim 15 wherein said active compound is N-acetyl-4-S-cysteaminylphenol.

35. An anti-melanoma composition of claim 15 wherein said active compound is α-methyl-4-S-cysteaminylphenol.

36. A topical pharmaceutical composition of claim 20 wherein $R_1$ is $C_1$ to $C_8$ alkyl and $R_2$ and $R_3$ are H.

37. A topical pharmaceutical composition of claim 20 wherein $R_3$ is $C_1$ to $C_8$ alkanoyl and $R_1$ and $R_2$ are H.

38. A topical pharmaceutical composition of claim 20 wherein said active compound is α-methyl-4-S-cysteaminylphenol.

* * * * *

UNITED STATES PATENT AND TRADEMARK OFFICE
CERTIFICATE OF CORRECTION

PATENT NO. : 5,395,611

DATED : March 7, 1995

INVENTOR(S) : Kowichi JIMBOW

It is certified that error appears in the above-identified patent and that said Letters Patent is hereby corrected as shown below:

Claim 2, col. 16, line 22, "cysteaminylphenol, 4-S-". occurrence); and
                line 23, delete "homo-cysteaminylphenol".

Claim 38, col. 18, line 59, delete "20" and insert therefor --21--.

Signed and Sealed this

Fifth Day of September, 1995

*Attest:*

BRUCE LEHMAN

*Attesting Officer*        *Commissioner of Patents and Trademarks*